(12) United States Patent
Madsen et al.

(10) Patent No.: US 10,620,095 B2
(45) Date of Patent: Apr. 14, 2020

(54) APPARATUS AND METHODS FOR DETECTING ANALYTES

(71) Applicant: Nexus Dx, Inc., San Diego, CA (US)

(72) Inventors: Randall D. Madsen, San Diego, CA (US); Robert Klepper, San Diego, CA (US)

(73) Assignee: NEXUS DX, INC., San Diego, CA (US)

(*) Notice: Subject to any disclaimer, the term of this patent is extended or adjusted under 35 U.S.C. 154(b) by 0 days.

(21) Appl. No.: 15/816,507

(22) Filed: Nov. 17, 2017

(65) Prior Publication Data

US 2018/0180519 A1    Jun. 28, 2018

Related U.S. Application Data

(63) Continuation of application No. 14/164,603, filed on Jan. 27, 2014, now Pat. No. 9,823,172, which is a continuation of application No. PCT/US2012/048526, filed on Jul. 27, 2012.

(60) Provisional application No. 61/512,277, filed on Jul. 27, 2011.

(51) Int. Cl.
    *G01N 33/53*    (2006.01)
    *G01N 1/28*    (2006.01)
    *B01L 3/00*    (2006.01)

(52) U.S. Cl.
    CPC .............. *G01N 1/28* (2013.01); *B01L 3/5082* (2013.01); *B01L 3/527* (2013.01); *G01N 33/5302* (2013.01); *B01L 3/5023* (2013.01); *B01L 2200/027* (2013.01); *B01L 2200/16* (2013.01); *B01L 2300/046* (2013.01); *B01L 2300/0609* (2013.01)

(58) Field of Classification Search
    None
    See application file for complete search history.

(56) References Cited

U.S. PATENT DOCUMENTS

| | | | |
|---|---|---|---|
| 3,583,609 | A | 6/1971 | Oppenheimer |
| 4,320,087 | A | 3/1982 | Chau et al. |
| 5,171,537 | A | 12/1992 | Wainwright |
| 6,325,968 | B1 | 12/2001 | Fricker |
| 8,007,745 | B2 | 8/2011 | Clark et al. |
| 2001/0030205 | A1 | 10/2001 | Nybakke |
| 2003/0219905 | A1 | 11/2003 | Clark |

(Continued)

FOREIGN PATENT DOCUMENTS

| | | |
|---|---|---|
| CN | 101393090 A | 3/2009 |
| DE | 34 12 886 A1 | 10/1984 |

(Continued)

OTHER PUBLICATIONS

Coligan, John E., et al., [Eds.] 1999, Current Protocols in Immunology, vol. 1-6, pp. 6036.

(Continued)

*Primary Examiner* — Erik B Crawford
(74) *Attorney, Agent, or Firm* — Knobbe, Martens, Olson & Bear, LLP

(57) ABSTRACT

The present invention provides an apparatus for retaining solid state reagents and/or for processing sample for a diagnostic test, where the apparatus avoids liquid "hang-up" that would otherwise result in loss of sample or fluid volume during sample transfer. The invention further provides diagnostic methods that employ the apparatus, so as to provide sensitive and accurate analyte detection.

16 Claims, 16 Drawing Sheets

(56) References Cited

U.S. PATENT DOCUMENTS

| | | |
|---|---|---|
| 2004/0261902 A1 | 12/2004 | Eddins |
| 2005/0123948 A1 | 6/2005 | Claycomb |
| 2008/0199851 A1 | 8/2008 | Egan |
| 2009/0023146 A1 | 1/2009 | Harnack et al. |
| 2010/0323343 A1 | 12/2010 | Egan |
| 2014/0008376 A1 | 1/2014 | Whitaker et al. |

FOREIGN PATENT DOCUMENTS

| | | |
|---|---|---|
| JP | S54-104384 A | 1/1979 |
| JP | S59-188560 A | 10/1985 |
| JP | 2004-004078 A | 1/2004 |
| WO | WO 94/27719 | 12/1994 |
| WO | WO 2007/098184 A2 | 8/2007 |
| WO | WO 2009/014787 A2 | 1/2009 |
| WO | WO 2010/132453 A2 | 11/2010 |

OTHER PUBLICATIONS

Maesoon, et al. "A robust superhydrophobic and superoleophobic surface with inverse-trapezoidal microstructures on a large transparent flexible substrate." Soft Matter 6.7 (2010): 1401-1404.

Dunn, David A., et al., "Challenges and solutions to ultra-high-throughput screening assay miniaturization: submicroliter fluid handling." Drug discovery today 5 (2000): S84-S91.

International Search Report dated Oct. 1, 2012 in International Application No. PCT/US 2012/48526.

Office Action dated Oct. 24, 2014 in Chinese Application No. 201280047374.8, filed Jul. 27, 2012.

European Communication dated Dec. 22, 2014 in European Application No. 12817417.4 filed Feb. 18, 2014.

Examination Report dated Feb. 2, 2016 in European Application No. 12817417.4.

Office Action dated Mar. 25, 2016 in Chinese Patent Application No. 201280047374.8.

Office Action dated May 24, 2016 in Japanese Patent Application No. 2014-523061.

Examination Report dated Aug. 26, 2016 in European Application No. 12817417.4.

Office Action dated Dec. 16, 2016 in Chinese Patent Application No. 201280047374.8.

Decision of Rejection dated May 8, 2017 in Japanese Patent Application No. 2014-523061.

European Communication dated Jul. 5, 2017 in European 12817417.4 filed Feb. 18, 2014.

APPARATUS AND METHODS FOR DETECTING ANALYTES

This application is directed generally to an apparatus and method for analyte detection, and is related to the apparatus and methods described in WO 2007/098184, WO 2009/014787, and WO 2010/132453, each of which is hereby incorporated by reference in its entirety. This application is a continuation application of the U.S. patent application Ser. No. 14/164,603 filed on Jan. 27, 2014, now issued as U.S. Pat. No. 9,823,172, which claims the benefit of priority of the international patent application, PCT/US2012/048526, filed on Jul. 27, 2012, which claims the benefit of priority of the U.S. Provisional Patent Application No. 61/512,277, filed on Jul. 27, 2011. More particularly, but not exclusively, the application relates to an apparatus or kit for retaining specific binding agents in solid form, and for processing samples of interest with the agents prior to detection of the target analyte(s). The apparatus is configured for retention of solid state reagent beads or pellets while allowing unhampered sample transfer.

BACKGROUND

Field of the Invention

Assays for detecting the presence or level of substances ("analytes") in biological or environmental samples often involve antigen-antibody reactions, and may involve capture and detection of immunocomplexes in a lateral flow assay format. Tests may be designed for a quantitative, semi-quantitative, or qualitative determination.

Because of the often small concentration of the analyte of interest in the test fluid and/or the small volume of test fluid, the assay must guard against sample loss, especially where the test requires significant sample manipulation and/or is intended to be quantitative in nature. For example, in the assay described in WO 2007/098184 and WO 2009/014787, the apparatus involves solid-state immunoreagent beads retained in a tube compartment for solubilization or processing with a liquid sample containing the analyte of interest. Once the analyte is bound by the solubilized immunoreagents, the sample is delivered to a lateral flow membrane for immunocomplex capture and detection. However, given that the volume of many liquid samples is in the milliliter or microliter range, the test should guard against sample loss during transfer to maintain sensitivity and/or accuracy. The present invention meets these and other objectives.

SUMMARY OF THE INVENTION

The present invention provides an apparatus or kit for retaining solid-state reagents and/or for processing samples for a diagnostic test, where the apparatus avoids liquid "hang-up" or retension that would otherwise result in loss of sample or loss of fluid volume during sample transfer. The invention further provides diagnostic methods that use the apparatus to provide sensitive and accurate analyte detection.

In one aspect, the invention provides an apparatus or kit comprising a sample processing component, or "reagent tube." The reagent tube includes a compartment containing solid-state reagents, which may be in dry (or dried) bead, pellet, or wafer form. The compartment is generally designed to hold, and transfer, milliliter or microliter-sized fluid samples. The compartment has an opening formed by a rib design sufficient to retain the solid-state reagents, while allowing for the addition of a liquid sample to the compartment for solubilization of the reagents and/or binding with one or more analytes. The rib design reduces hang-up of liquid sample during sample transfer into and/or out of the compartment. The positioning of the ribs in the reagent tube may vary, but they are generally positioned such that, in at least one step of the assay, a liquid sample is transferred into and/or out of the compartment through the opening defined by the ribs. Exemplary rib designs and dimensions for the apparatus are disclosed herein. For example, the ribs may have a rounded cross-section, and in some embodiments, have a diameter or cross-section of from about 0.01 to about 0.06 inches, such as in the range of 0.02 to 0.05 inches. The rib design in certain embodiments does not include, or minimizes, sharp angles. In some embodiments, where the ribs are placed at the bottom or floor of the tube, the ribs protrude from the end of the tube. The rib design may have three or four ribs in some embodiments, and these may be approximately evenly spaced in a radial pattern or substantially parellel pattern over the compartment opening. While the ribs may intersect in the center of the compartment opening, in some embodiments, the ribs do not intersect or meet.

As used herein, the term "solid-state reagents" refers to reagents not solubilized in liquid form, and thus includes reagents in lyophilized, dried, or powdered form, as well as reagents conguated to a solid support, such as a bead. In certain embodiments, the solid-state reagents are immunoreagents. The immunoreagents may be lyophilized or dried, and/or compressed in the form of one or more pellets, beads, wafer, and/or pills, and optionally combined with one or more suitable binders or other compounds to affect the properties of the solid state, including subsequent solubilization. In some embodiments, the immunoreagents are conjugated to one or more beads. The immunoreagents may comprise at least one antibody against the analyte of interest, or at least one antibody against each analyte of interest where the assay tests for a plurality of analytes. In some embodiments, the immunoreagents are designed to form a "sandwich immunoassay" in the presence of analyte, and in these embodiments the immunoreagents are provided in pairs for each analyte. For each "pair," at least one immunoreagent is specific for the analyte of interest and comprises, in addition to an antibody or antigen-binding portion thereof, a linked binder or immobilization moiety, such as a biotin or streptavidin, or an oligonucleotide. The immobilization moiety allows for immobilization of the resulting immunocomplex for detection. Each pair further comprises at least one immunoreagent having an attached detectable moiety, such as a fluorescent moiety or visually observable moiety, to enable detection of the immobilized immunocomplex. Immunocomplexes may be captured and detected in a lateral flow detection format, as described in detail herein, and may be detected with the aid of a reader instrument.

The container is designed such that one or more liquid samples, which may include extraction buffers and samples containing the analyte of interest, may be added to the compartment, e.g., by pipette. After solubilization and/or binding of the reagents, the sample is transferred to a second device for detection. In some embodiments, the apparatus further comprises a cap fitting over the opening of the container or tube, which aids in the delivery of the liquid sample from the compartment to a detection device or "Test Device" (TD). In still other embodiments, the reagent tube has a mechanism to controllably deliver a liquid sample from the floor of the compartment. This mechanism or the cap may include a component to tightly interface with a port on a test device.

The apparatus may, of course, include other components or implements such as a sample collecting implement, sample processing and/or extracting components, and/or a reader instrument.

In other embodiments, the invention provides a method for detecting an analyte. The method may employ an apparatus of the invention. For example, the method may comprise applying a liquid sample suspected of containing the analyte to the reagent tube. After simple mixing or agitation sufficient to solubilize and/or bind the solid state reagents with analyte or analytes in the liquid sample, the reagent tube is interfaced with a detection device, such as a lateral flow membrane in some embodiments. The interface may be by means of an attachable cap or other interfacing mechanism included within the design of the reagent tube. After transferring the liquid sample to the detection device, the presence of analyte may be read by visual inspection or by the use of a reader instrument. Because of the presence of the rib design, the volume of liquid sample delivered during the various steps remains consistent with the volumes delivered to the solid-state reagents.

Additional aspects are further described below in conjunction with the appended drawings.

BRIEF DESCRIPTION OF THE DRAWINGS

The present application may be more fully appreciated in connection with the following detailed description taken in conjunction with the accompanying drawings, wherein.

DETAILED DESCRIPTION OF THE INVENTION

Figure 1A:
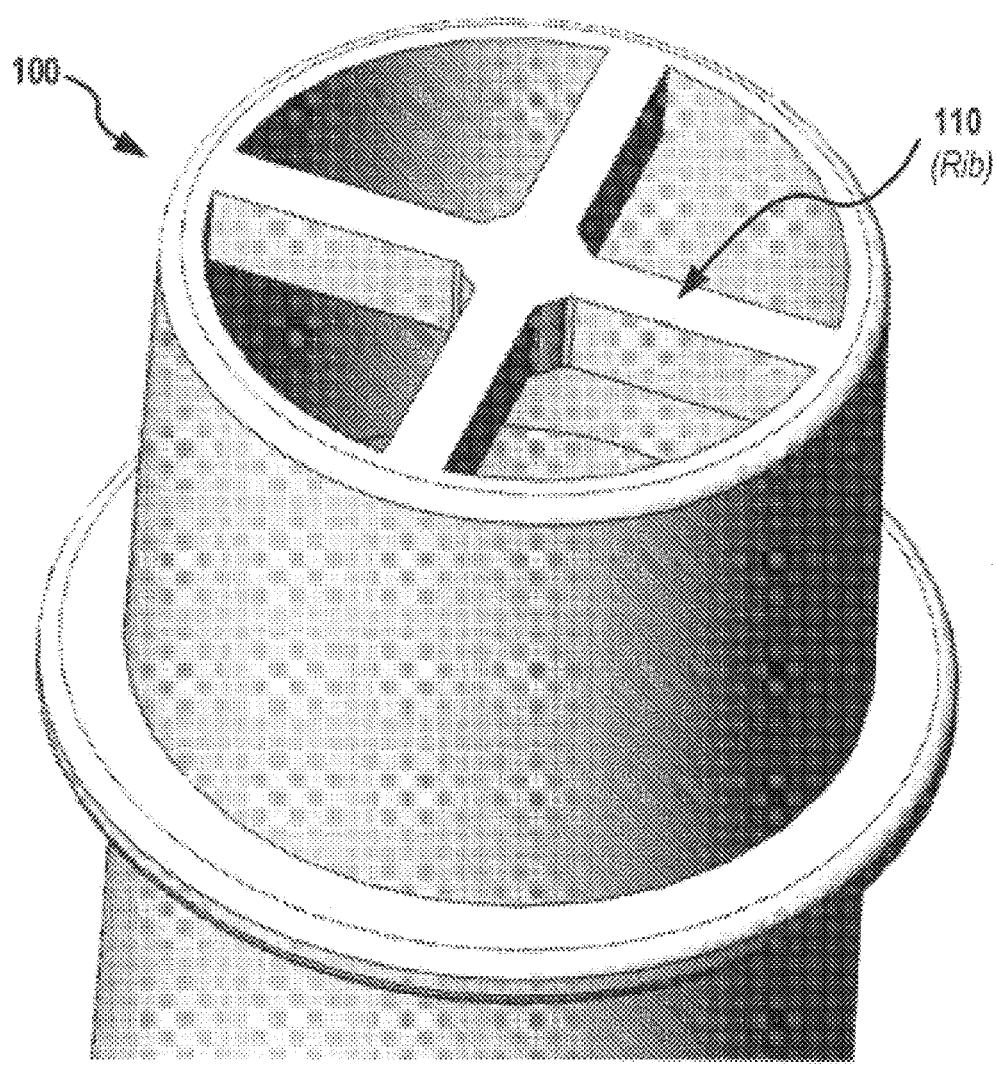
FIGS. 1A and 1B illustrates a sample collection tube with ribs for retention of reagents (FIG. 1A), and illustrates exemplary cross-sectional dimensions of 0.03 inches×0.04 inches (FIG. 1B).

The present invention provides an apparatus or kit for retaining solid state reagent forms and/or for processing a sample for a diagnostic test, where the apparatus avoids liquid "hang-up" that would otherwise result in loss of sample, or loss of fluid volume, or inconsistent fluid retention during sample transfer. The invention further provides diagnostic methods using the apparatus to provide sensitive and accurate analyte detection.

As described herein, the kit or apparatus avoids "hang-up" or loss of liquid sample upon transfer to or from the compartment, and provides consistent transfer volumes between tests. For example, when using microliter-sized samples (e.g., in the range of 100 to 500 µl, or in the range of 150 to 400 µl), the rib design results in "hang-up" or loss of no more than 30 µl, 25 µl, or 20 µl, in certain embodiments. For example, depending on the volume of a particular sample, sample hang-up or loss may be less than 20% of the sample volume, less than 15% of the sample volume, less than 10% of the sample volume, or less than 5% of the sample volume. In certain embodiments, with consistent sample volume sample loss does not vary by more than 10% between samples, or more than 5% between samples.

In various embodiments, the apparatus or kit comprises a reagent container or reagent tube, that retains the solid-state reagents for processing with a liquid sample. The apparatus or kit may further comprise additional components for the diagnostic assay, such as one or more of a sample collection implement (e.g., cotton swab, brush, woven substrate, etc.), sample tube for extraction of sample with assay media, assay media appropriately selected for extraction and suspension of the analyte(s) of interest, pipette for transfer of sample, test device for capturing and detecting the presence of analyte (e.g., a lateral flow test device), and a reader instrument (e.g., where the detection label is not designed for mere visual inspection or where quantitative detection is required). These additional components are described in detail herein.

Generally, the reagent tube is a container designed such that one or more liquid samples are added to the solid state reagents by pipette or other means. The liquid sample can be added after extraction of a biological or environmental sample with extraction solution or media to create the liquid sample. Alternatively, the extraction of the sample and solubilization of the binding reagents can take place simultaneously. While the term "tube" is used herein for convenience, the reagent tube is not limited to a conventional tube shape, but refers to any container sufficient to retain the reagents as described. After solubilization and/or binding of the solid state reagents with liquid sample, the resulting test sample is subsequently delivered to a test device for detection. In some embodiments, the test device comprises a solid support for immobilizing captured analyte for detection. The test device may be in the form of lateral flow membrane.

In some embodiments, the kit comprises a cap fitting over the opening of the reagent tube, to aid in the delivery of the test sample to the detection device upon inversion of the reagent tube. These embodiments are described, for example, in WO 2009/014787, which is hereby incorporated by reference in its entirety. In still other embodiments, the reagent tube has a built-in mechanism for controllably delivering the test sample from the floor of the compartment to the test device without inversion of the device. These embodiments are described, for example, in WO 2007/098184, which is hereby incorporated by reference in its entirety. This mechanism or the cap may include a mechanism to interface with a port on a lateral flow device, as described in WO 2010/132453, which is hereby incorporated by reference.

Reagent Beads, Wafers, and Pellets

The reagent tube comprises a compartment for retaining solid state binding reagents. In various embodiments, the solid state reagents are in bead, wafer, or pellet form, and comprise reagents for an immunoassay ("immunoreagents"). The solid reagents may be in the form of, for example, a pill, bead, lyophilized pellet, pressed lyophilized power, or may be dried or conjugated on a solid support (e.g., a bead). Preparing immunoreagents and immunoconjugates is known in the art, for example, see CURRENT PROTOCOLS IN IMMUNOLOGY (Coligan, John E et al., eds 1999).

The compartment may comprise from 1 to about 10 reagent beads, or in some embodiments, from about 2 to about 5 reagent beads.

In various embodiments, the immunoreagents comprise at least one antibody against the analyte of interest, or at least one antibody against each analyte of interest where the assay tests for a plurality of analytes. At least one immunoreagent may comprise a capture or detectable moiety as described herein. In some embodiments, the immunoreagents are designed to form a "sandwich immunoassay" in the presence of analyte, and are therefore provided in pairs for each analyte. In these embodiments, at least one immunoreagent comprises a capture moiety, such as a polynucleotide-based capture moiety, which is capturable by a corresponding moiety in the test device. In various embodiments, at least one immunoreagent comprises a detectable moiety, which may be visually detected, or detected with the aid of an instrument.

In one embodiment, at least one immunoreagent is a capturable reagent that comprises a capture moiety. The capturable reagent comprises an antibody or immunoreagent that is linked, directly or indirectly, to a capture moiety partner. The capture moiety partner is "captured" by a cognate-immobilized capture moiety partner disposed on a solid support (e.g., nitrocellulose membrane) as an addressable region or line in the Test Device. Such capture moiety and cognate partner are referred to herein as Capture Moiety Partners (CMP(s)). In exemplary embodiments, a CMP can comprise a first pRNA molecule of a particular sequence, and which binds to a second pRNA molecule complementary to the first molecule, allowing specific binding of the two molecules when they come into contact with each other. In various embodiments, a CMP comprises molecules including but not limited to pRNA or pDNA molecules, an aptamer and its cognate target, or streptavidin-biotin, or other ligand/receptor pair. For a given set of CMPs, the two molecules are related in the sense that their binding with each other is such that they are capable of distinguishing their binding partner from other assay constituents having similar characteristics.

The immunoreagents may form an immunocomplex in the presence of an analyte, which may be selected from any analyte of interest in biological or environmental samples, including microorganisms and markers indicative thereof. For example, in some embodiments, the different analytes detected are viruses or components of viruses. In various embodiments, the different antigens are from influenza viruses and/or subtypes of influenza virus. In yet other embodiments, the different analytes detected are one or more different infectious agents and/or one or more different subtypes of an infectious agent.

The size of the reagent bead or pellet is selected so as to be retained by the rib or "cross-hair" design. For example, the bead or pellets may have a cross-section or diameter of from about 1 mm to about 5 mm, such as about 2 mm or about 3 mm in certain embodiments.

Reagent Tube and Rib Designs

In one aspect, the invention provides an apparatus or kit comprising a reagent tube retaining the solid state reagents in bead or pellet form in a compartment. The compartment has an opening formed by a rib design sufficient to retain the solid state reagents while allowing unhampered sample transfer or flow, that is, reducing hang-up of liquid sample. The reagent tube further provides for ease of washing, especially in embodiments employing reagents conjugated to solid supports.

The compartment houses the reagents, and is sufficient to hold and transfer a liquid sample in the range of about 50 µl to about 10 mLs. In some embodiments, the volume of the compartment may hold and transfer from about 100 µl to about 5 mL, about 2 mL, about 1 mL, about 0.5 mL, or about 0.2 mL.

In some embodiments, the ribs are rounded, and do not contain sharp angles, since sharp angles may lead to fluid hang-up. The rib design may have three or four ribs in some embodiments, and these may be evenly spaced in a radial pattern over the opening of the compartment. For example, the ribs may form a cross pattern. Of course, other alternative patterns are possible, such as a substantially parallel pattern of ribs. The design should, however, minimize the amount of rib surface area. For example, the ribs may have a rounded cross-section, and in some embodiments, may have a diameter or cross-section of from about 0.01 to about 0.06 inches, such as about 0.02, about 0.03, or about 0.04 inches.

In some embodiments, where the rib design separates the compartment (or bottom chamber) from the end of the tube, the ribs protrude from the end of the tube when viewed from the side.

While the ribs may intersect in the center of the compartment opening, in some embodiments the ribs do not intersect or meet.

In some embodiments, the surface of the tube and/or ribs is modified to decrease surface tension, e.g., by silanization.

Figure 1B:
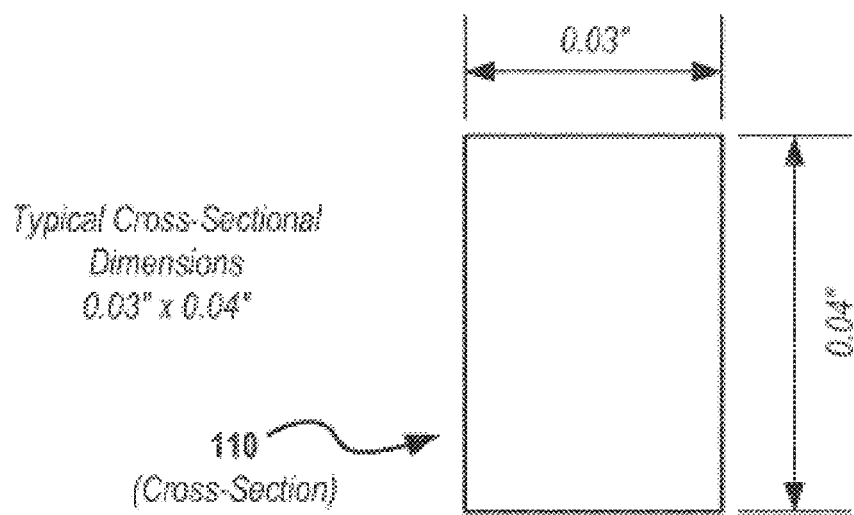

Attention is now directed to FIG. 1A, which illustrates a sample reagent tube 100. Tube 100 is used to store a liquid sample including a reagent. Tube 100 includes four crosshair ribs 110. The configuration shown creates a three-sided surface for a liquid sample to adhere to via surface tension. A cross-section of the ribs 110 is shown in FIG. 1B, which has a rectangular shape with straight sides. Typical dimensions of the rib 110 cross section are 0.03 inches by 0.04 inches.

Figure 2A:
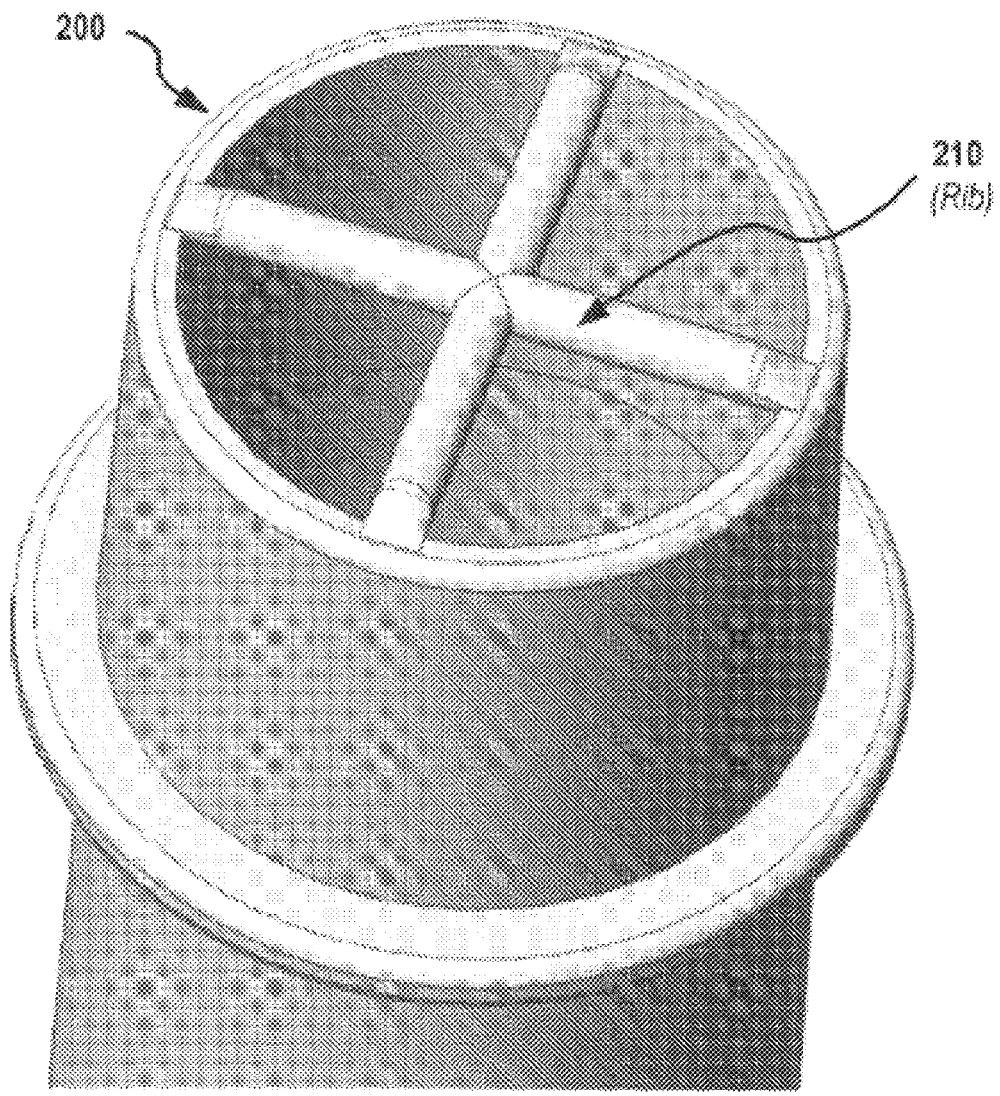
FIGS. 2A and 2B illustrate an exemplary rib design with rounded cross-section (FIG. 2A), and illustrates an exemplary cross-section of 0.03 inches (FIG. 2B).
Figure 2B:
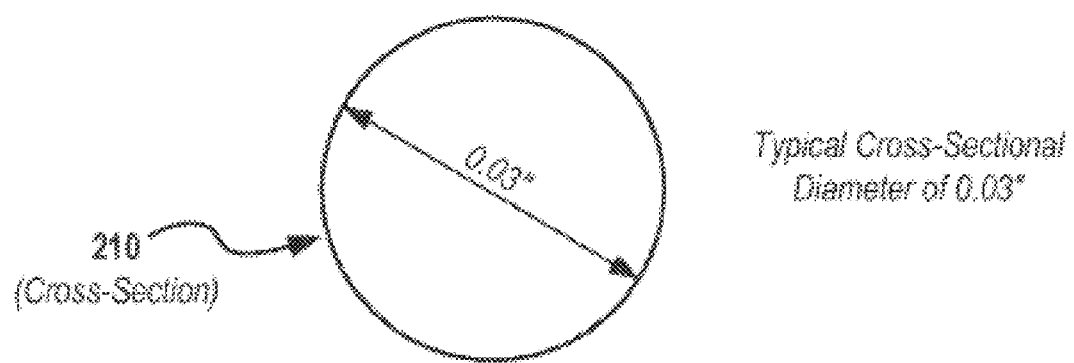

Attention is now directed to FIG. 2A, which illustrates details of an embodiment of a sample tube 200 in accordance with the present invention. Sample tube 200 includes a crosshair design having four ribs 210. Unlike the ribs in tube 100, ribs 210 are configured with a rounded cross-section as shown in FIG. 2B. In an exemplary embodiment, the cross-section of ribs 210 is round, however, other shapes, such as oval or other rounded-edge configurations, may alternatively be used in certain embodiments. Sample tube 200 is shown with four ribs 210, however, in some configurations more or fewer ribs may alternately be used (e.g., 3 ribs). In the embodiment of FIG. 2B, the ribs 210 have a diameter of 0.03 inches, however, different dimensions may be used in other embodiments.

Figure 3A:
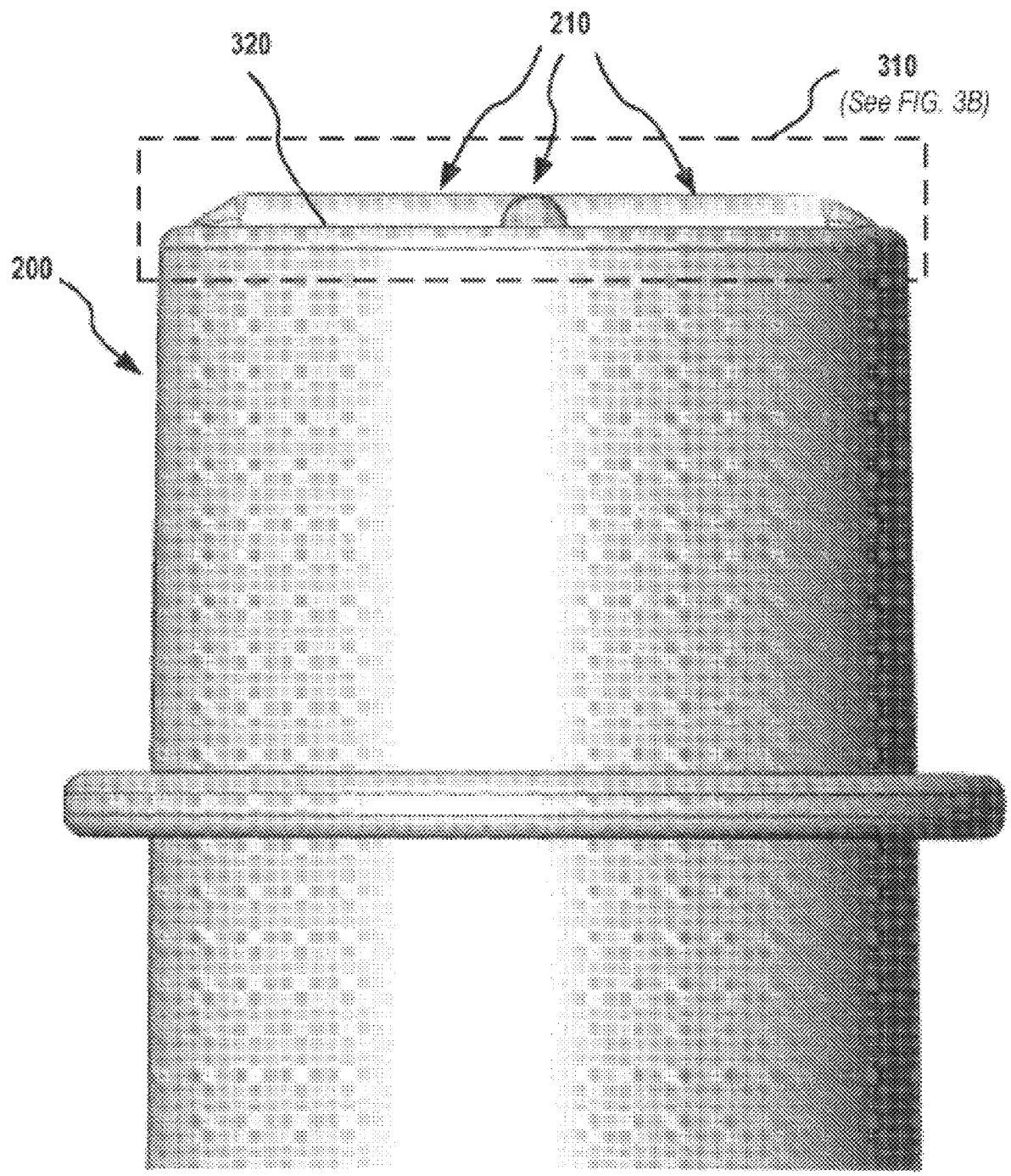
FIGS. 3A and 3B illustrate a side view (FIG. 3A) and a portion thereof (FIG. 3B) of an exemplary rib design that protrudes from the end of the tube.
Figure 3B:
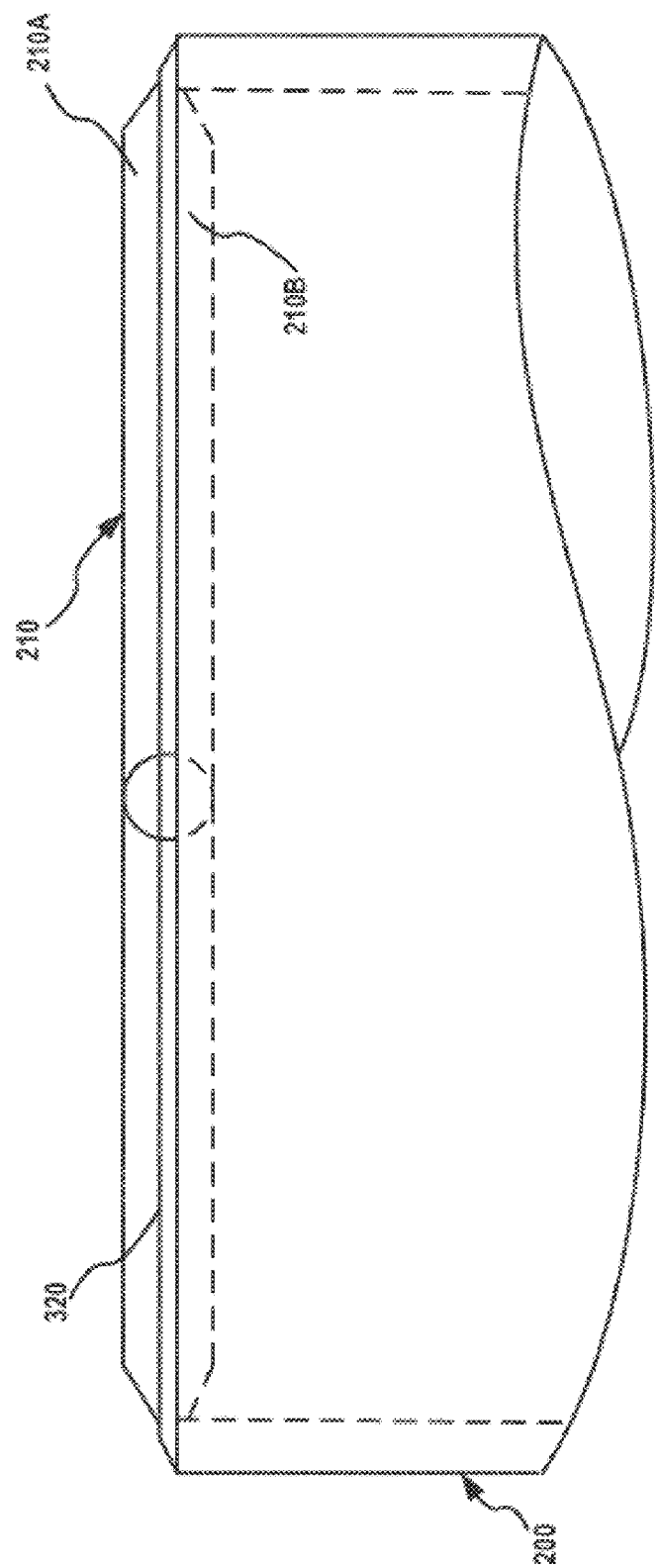

FIGS. 3A and 3B illustrate additional details of the embodiment shown in FIGS. 2A and 2B. FIG. 3A is a side view of a sample tube 200, including a top edge of the tube 320, and a plurality of ribs 210. Section 310 of sample tube 200, as shown in FIG. 3A, is further illustrated in FIG. 3B. In particular, ribs 210 may be positioned so that a first section of the ribs 210A is above the top edge 320, when viewed from the side as shown in FIG. 3A. In addition, a second section of the ribs 210B is below the top edge 320.

Figure 4:
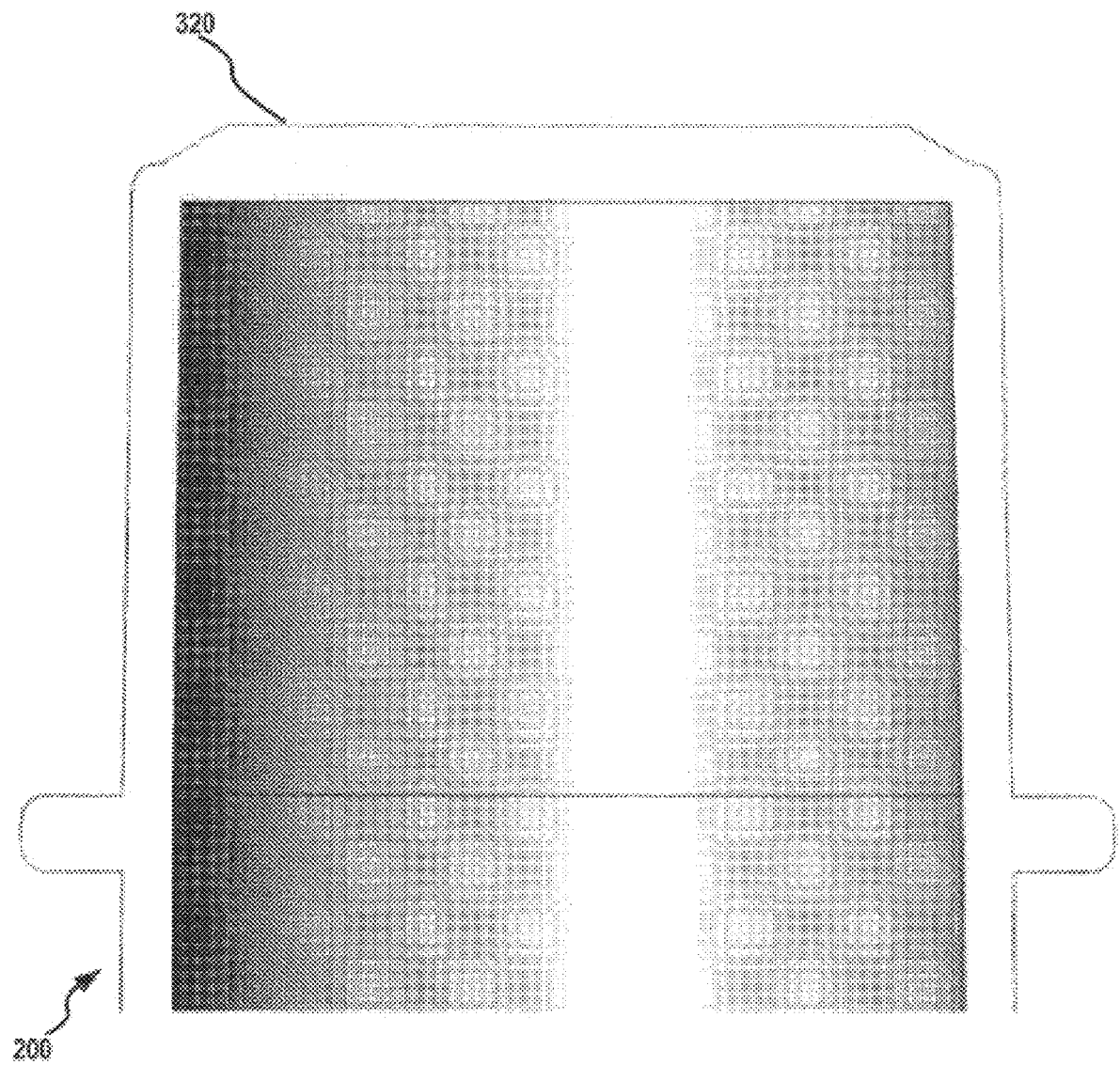
FIGS. 4 and 5 illustrate a cross-sectional side view (FIG. 4) and a perspective view (FIG. 5), including exemplary internal dimensions, of the reagent tube.

FIG. 4 illustrates a section view of the tube 200.

Figure 5:
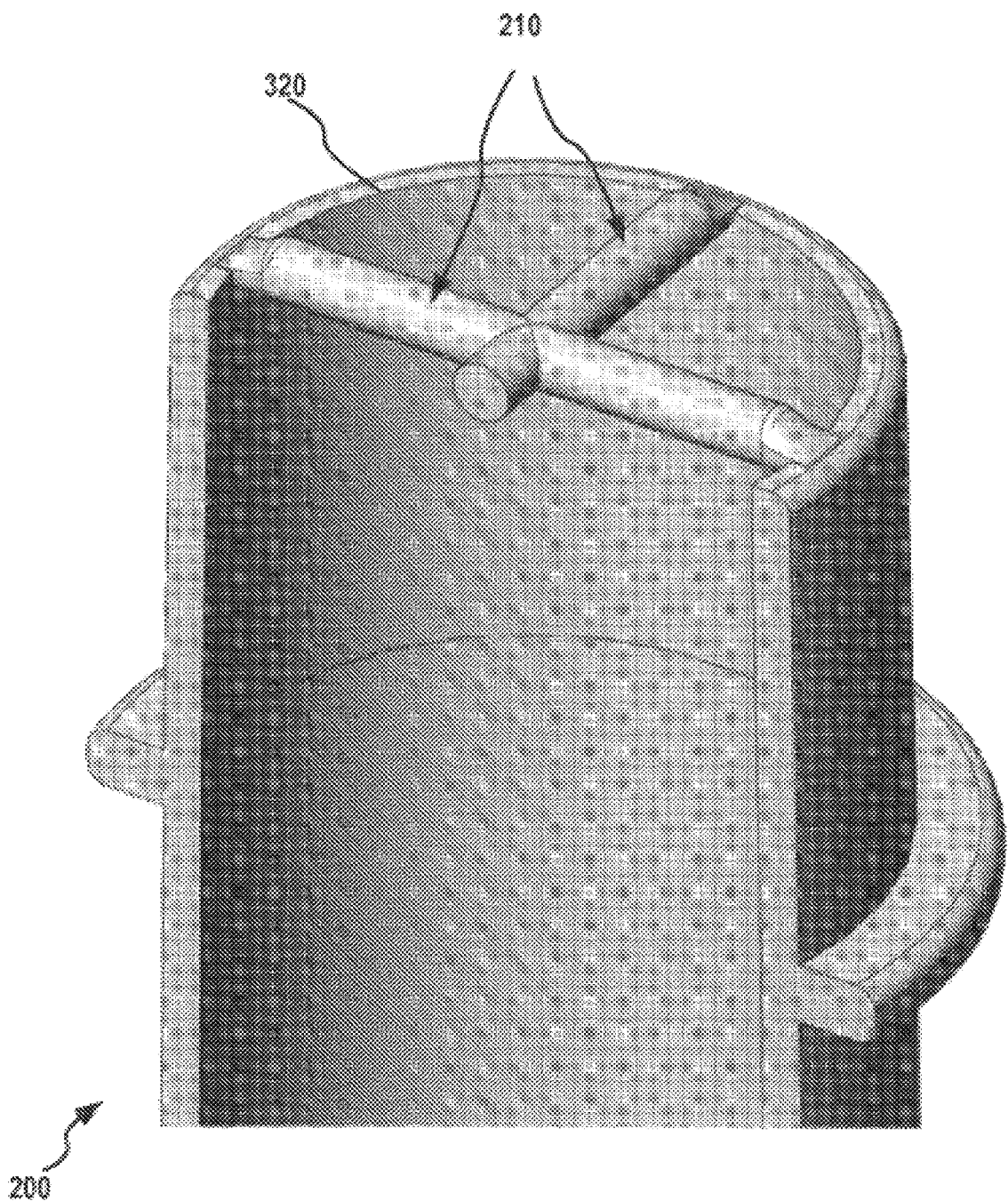

FIG. 5 illustrates an offset section view of tube 200, illustrating one configuration of ribs 210 positioned at the top edge of the tube.

Figure 6:
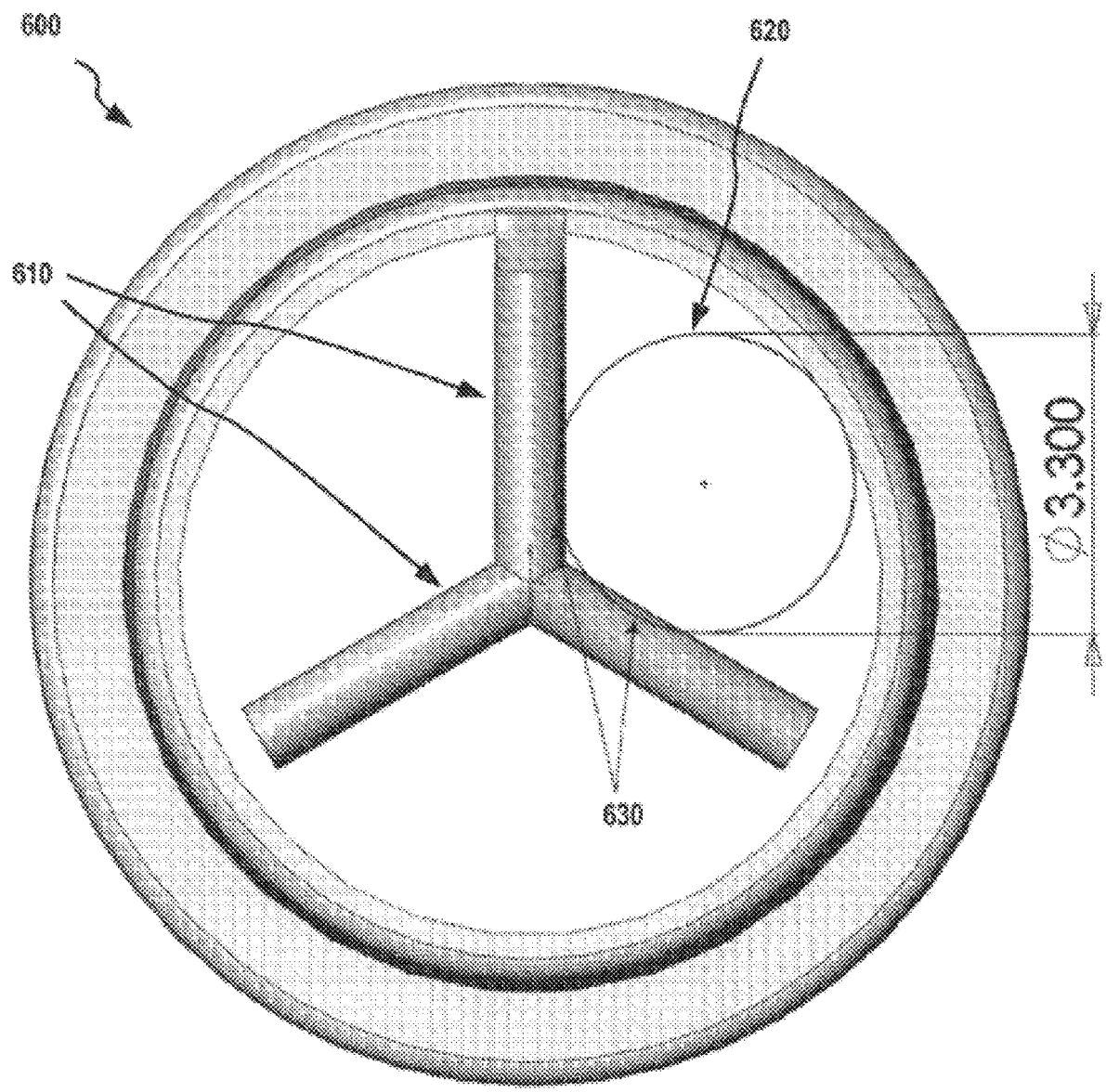
FIGS. 6 and 7 are top views illustrating exemplary rib designs having three ribs, spaced in a radial pattern.

FIG. 6 illustrates details of an embodiment of a sample tube 600 in accordance with aspects of the present invention. As shown in FIG. 6, sample tube 600 includes three ribs 610. Ribs 610 are configured so as to create three opening areas 620, where the openings 620 may be defined by a diameter as shown in FIG. 6, which may be related to the size of the beads used. In this example, the rib diameter is 0.03 inches, and the diameter of opening 620 is from about 1 mm to about 3 mm, but is also dependent on the size of the beads that are to be retained. For example, where the reagent beads or pellets are about 2 mm in cross-section, the size of the opening is sufficiently less than 2 mm. While this three-opening configuration creates minimal flow restriction, beads may be more likely to fall through the openings. To address this, the rib diameter may be increased, and/or the bead size may be adjusted based on the size of the opening, rib diameter, number of ribs, or other dimensional parameters.

Figure 7:
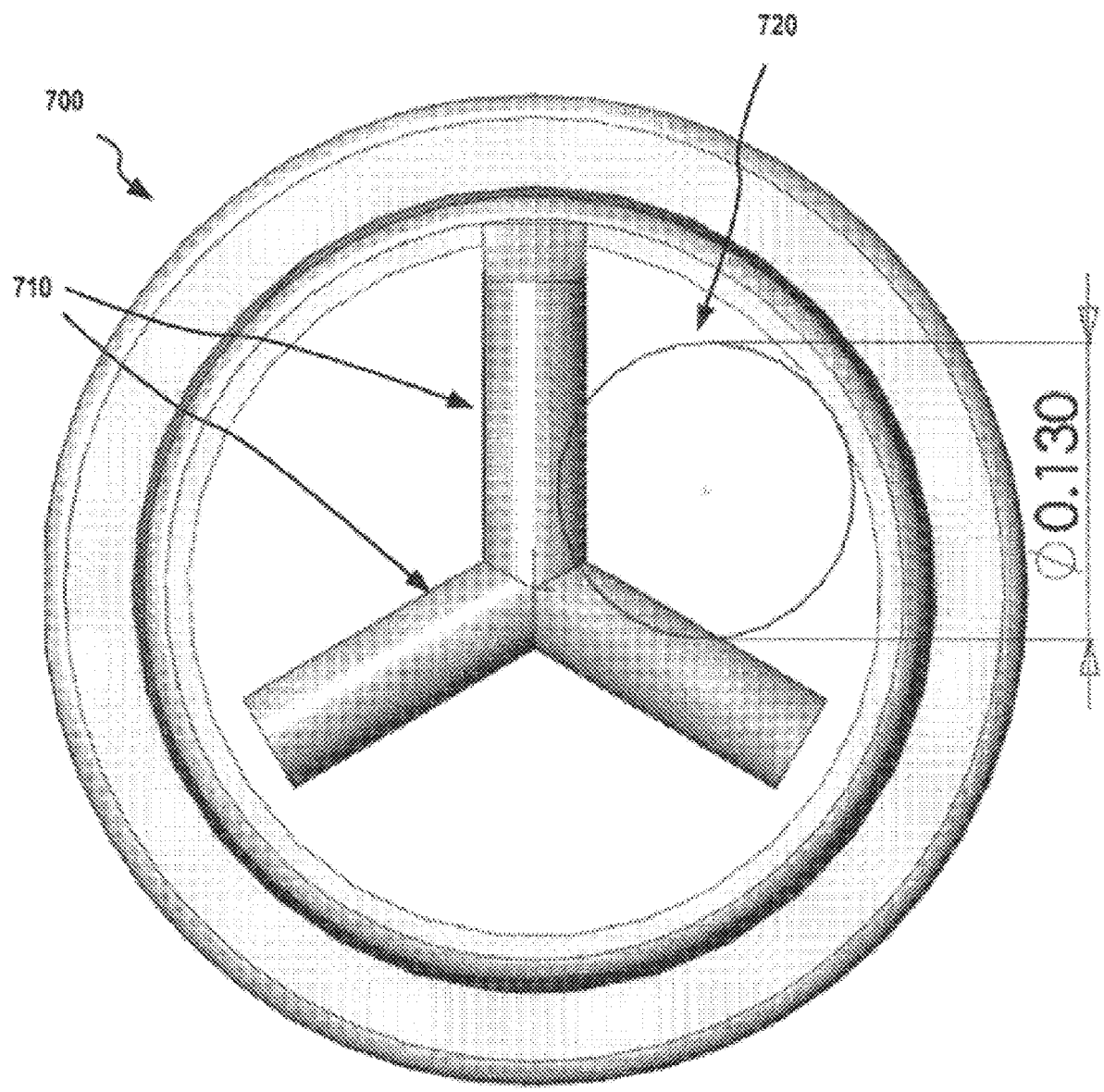

FIG. 7 illustrates another embodiment having larger diameter ribs 710. In this example, ribs 710 have a diameter of 0.045 inches, thereby creating a smaller opening 720.

Figure 8:
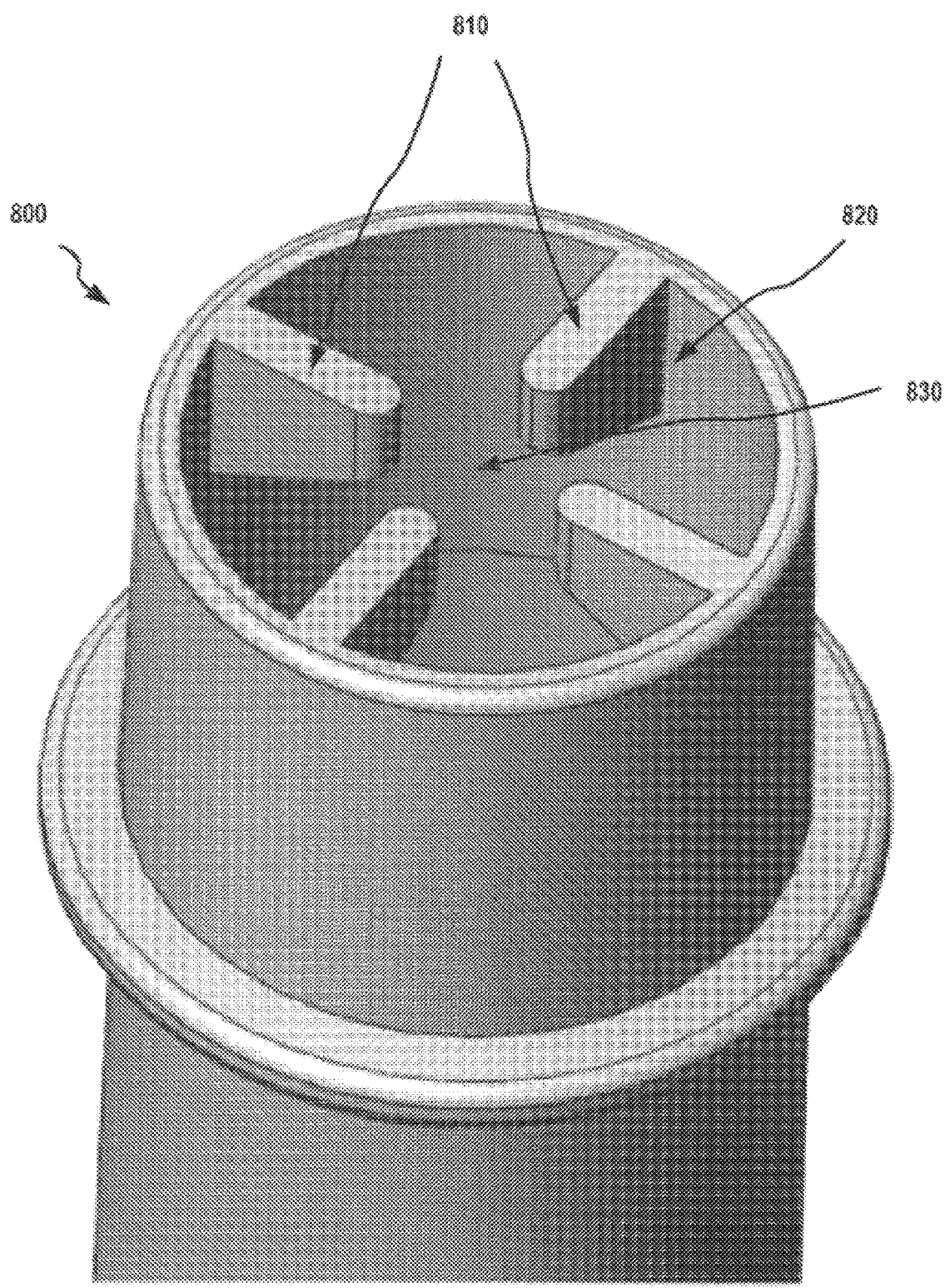
FIGS. 8 and 9 illustrate a perspective view (FIG. 8) and a top view (FIG. 9) of an exemplary rib design in which the ribs do not intersect.
Figure 9:
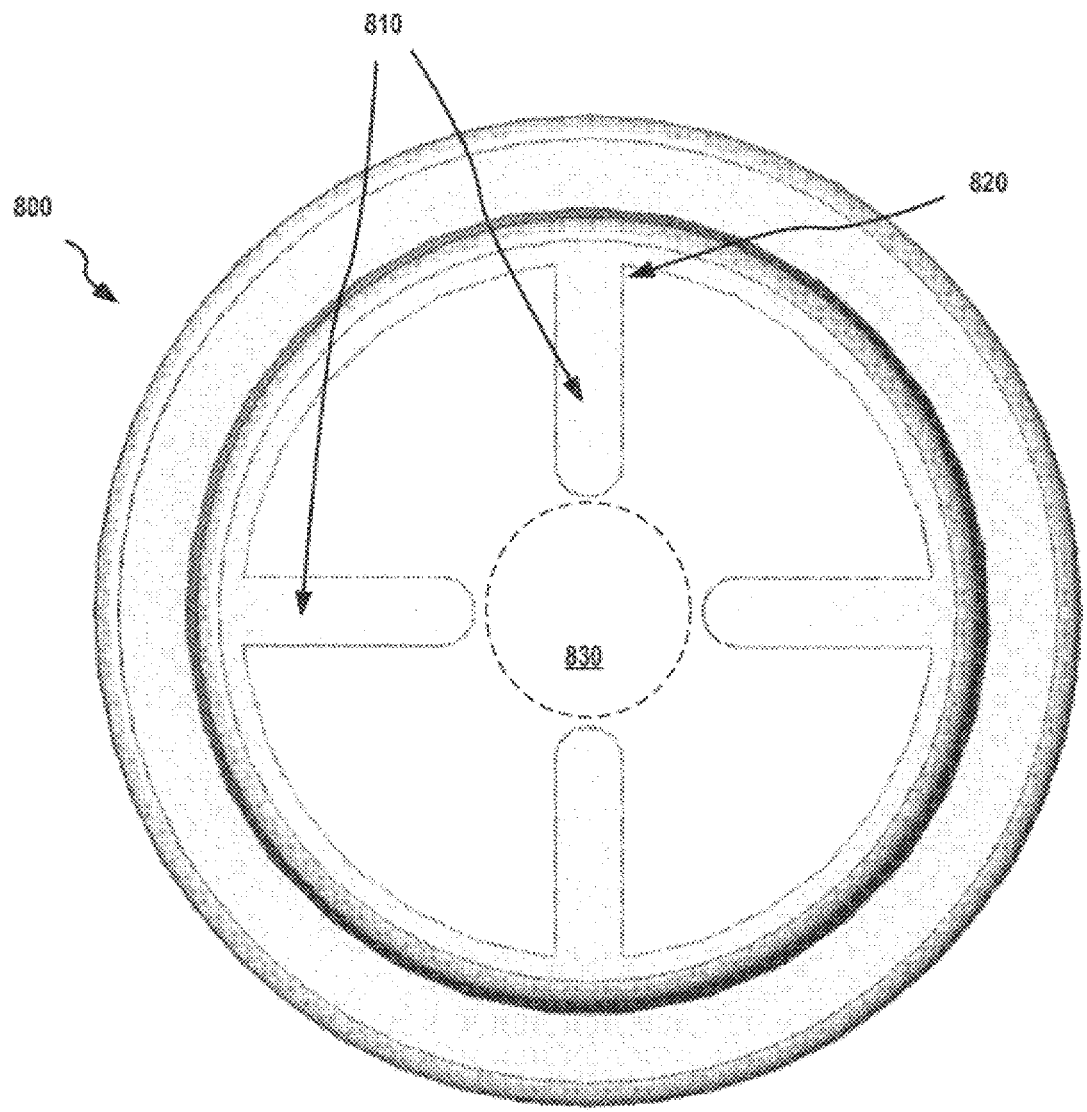

FIGS. 8 and 9 illustrate details of an embodiment of a sample collection tube 800 in accordance with aspects of the present invention. Tube 800 includes a plurality of buttressed ribs 810 (in this embodiment, four ribs 810 are shown, however, other embodiments may include more or fewer ribs). In some embodiments, rib edges 820 may be approximately square or right-angled, however, this may increase hold-up volume and increase sample variability. In some embodiments, rib edges 820 may be curved or rounded to provide better flow. As shown in FIGS. 8 and 9, the rib configuration may include an open center region 830 configured to allow flow through the middle, while also restricting flow of the beads through opening 830. In particular, the ribs may be configured so as to define opening 830 to be slightly smaller than the bead diameter.

Figure 10:
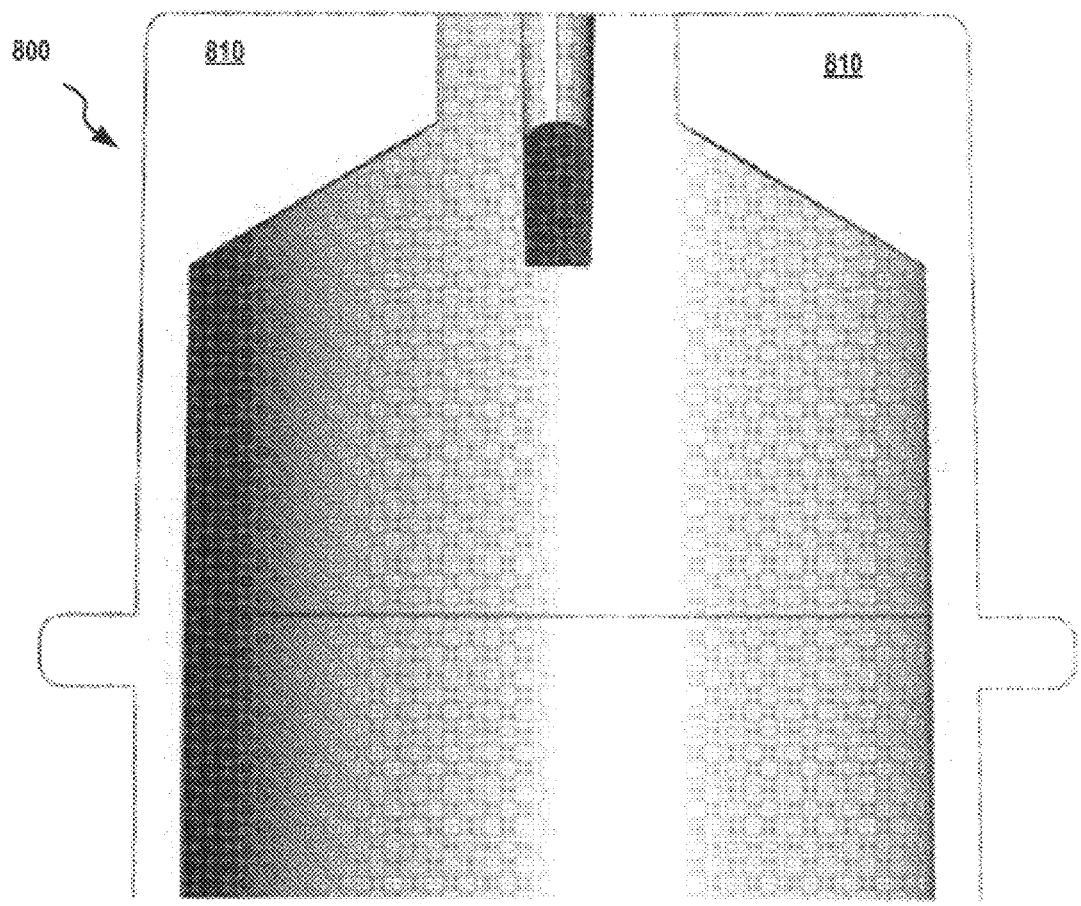
FIG. 10 illustrates a side, cross-sectional view of another exemplary rib design where the ribs do not intersect.

FIG. 10 is a cross-sectional side view of tube 800, showing a cutaway view of an embodiment of ribs 810.

Sample Processing and Transfer

The container is designed such that a liquid sample may be added to the compartment by pipette or other means, including releasing buffer from an upper chamber, and after solubilization and mixing of the reagents and analyte or analytes, the sample is transferred to a second device for detection. The pipette in certain embodiments is designed to transfer a specific volume of liquid sample, either by graduation marks or by other means for ensuring a particular volume of fluid transfer.

For optimal reaction of the reagents (e.g., immunoreagents) with analyte(s), mixing of the sample and reagents prior to detection is desired. Sufficient mixing of sample and binding agent may occur after about 5, 10, 15, 20, 25, 30, or 60 seconds, or more. For example, the mixing of sample and binding agent may be for from about 5 to 10 seconds, or about 10 to 15 seconds, or about 15 to 20 seconds, or about 20 to 30 seconds or about 30 to 60 seconds or greater. Mixing can be achieved by several methods, including flicking the reagent tube, wrist flicking the reagent tube, vortexing the tube, or rocking the reagent tube back and forth.

In some embodiment, the kit includes a means for assessing sufficient mixing. In certain embodiments, the reagent-sample mixing chamber further comprises a mixing indicator, which may be a dye incorporated into the reagent beads or pellets. Alternatively, the reagent beads can be coated or may contain a dye to indicate that proper mixing has occurred. For illustration, the reagent beads may be coated with a red dye, such that during mixing of the sample and binding agents in the presence of the beads, adequate contact and mixing is demonstrated by the solution turning a red color. Generally, the dye should be a releasable, water-soluble dye that is visible upon release to the naked eye.

In some embodiments, the kit includes a filter or membrane over the ribs to filter blood or other debris.

In some embodiments, the apparatus further comprises a cap fitting over the opening of the container or tube, which aids in the delivery of a liquid sample from the compartment to a detection device, upon inversion of the reagent tube. In still other embodiments, the reagent tube has a mechanism to controllably deliver a liquid sample from the floor of the compartment. This mechanism or the cap may include a component to tightly interface with a port on a lateral flow device.

Methods and Exemplary Embodiments

In other aspects, the invention provides a method for detecting an analyte. The method may employ an apparatus or kit of the invention as described herein. For example, the method may comprise applying a liquid sample suspected of containing the analyte to a reagent compartment or reagent tube retaining the solid-state binding reagents in bead or pellet form. Because the compartment has an opening formed by a rib design sufficient to retain the solid state reagents while reducing hang-up of liquid, the reagents are solubilized in the sample while minimizing sample loss when delivering the liquid sample to a detection device.

The apparatus or kit of the invention, as already described, may comprise the necessary components to collect a biological or environmental sample, as well as the reagents and buffers necessary to process and react with analytes in the sample so as to form complexes comprised of the specific binding reagents with their specific target analytes.

The method may be for the detection of any analyte(s) of interest in a biological or environmental sample. The sample is any material to be tested for the presence and/or concentration of one or more analytes. In general, a biological sample can be any sample taken from a subject, e.g., non-human animal or human. A biological sample can be a sample of any body fluid, cells, or tissue samples from a biopsy. Body fluid samples can include without any limitation blood, urine, sputum, semen, feces, saliva, bile, cerebral fluid, nasal swab, nasopharyngeal swab, nasopharyngeal aspirate, nasal wash, throat swab, urogenital swab, nasal aspirate, spinal fluid, etc. For example, a biological sample can be the plasma or serum fraction of a blood sample, protein or nucleic acid extraction of collected cells or tissues, or from a specimen that has been treated in a way to improve the detectability of the specimen, for example, a lysis buffer containing a mucolytic agent that breaks down the mucins in a nasal specimen significantly reducing the viscosity of the specimen and a detergent to lyse the virus thereby releasing antigens and making them available for detection by the assay.

The analyte of interest may be associated with a disease, pathologic or other physiological condition. In various embodiments, such analytes are biomarkers associated with a condition related to any body tissue, including but not limited to the heart, liver, kidney, intestine, brain, fetal tissue, or pancreas. Analytes include; but are not limited to, toxins, allergens, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof.

Figure 11:
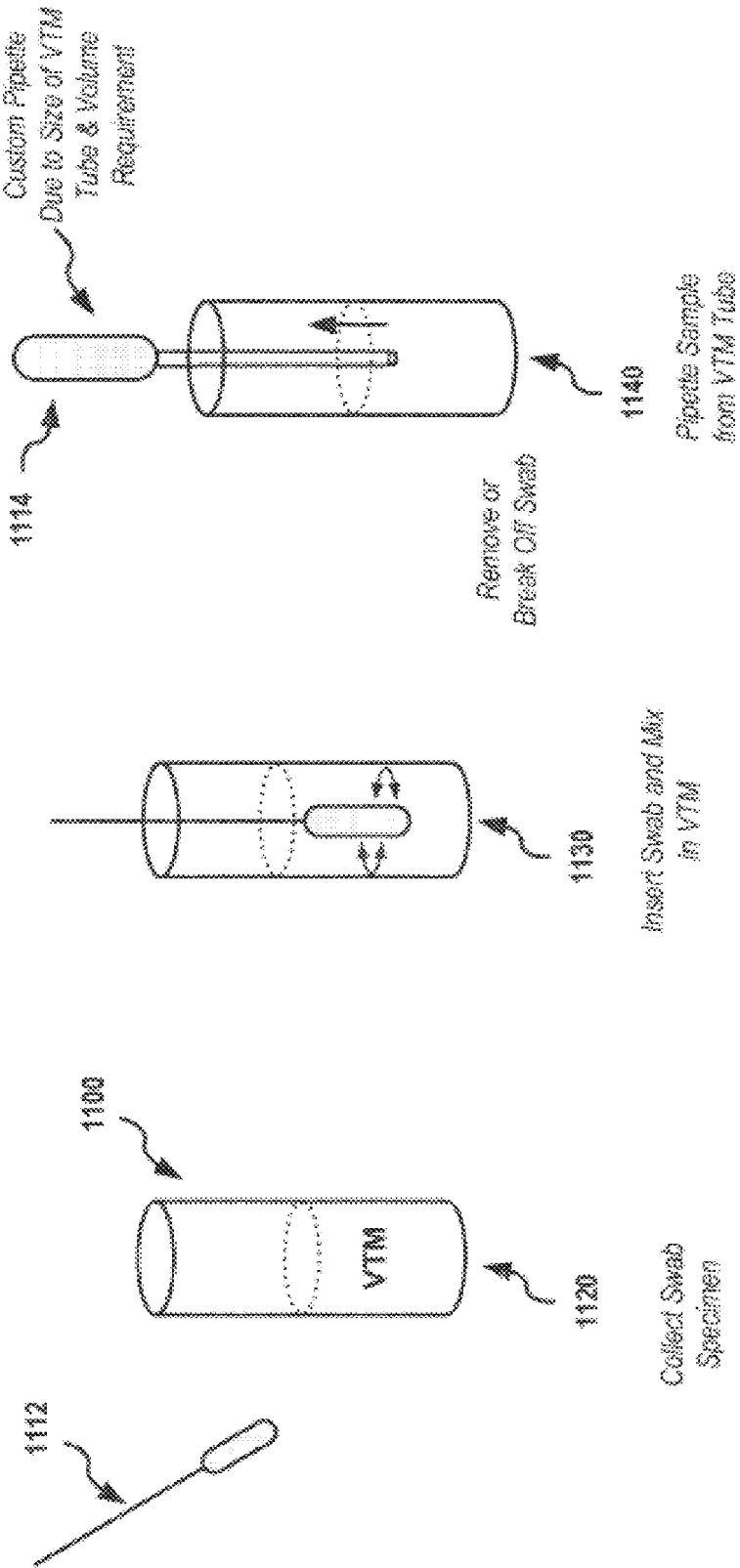
FIGS. 11 to 13 illustrate an exemplary method for detecting an analyte of interest, by processing a biological sample with assay medium (FIG. 11), followed by transfer to the reagent tube for processing with reagent beads (FIG. 12), and subsequent transfer of liquid sample to detection device (FIG. 13).

For illustration, in certain embodiments, the sample is extracted and contacted with solid form binding agents in separate kit components. For example, FIG. 11 illustrates an example processing sequence for use of a sample tube such as shown previously in FIGS. 1-10. A swab 1112 may be used to collect a sample, which is then placed in a sample collection tube 1100 at stage 1120. At stage 1130, the swab may be inserted into collection tube 1100, which includes an assay media appropriate for the analyte(s) of interest, such as Viral Transfer Media or VTM. The swab may then be rotated in tube 1100 to distribute the sample. At stage 1140, a pipette 1114 may be used to collect the sample from tube 1100. The pipette may be designed to transfer a specific volume of liquid sample, either by graduation marks or by other means for ensuring a particular volume of fluid transfer.

Figure 12:
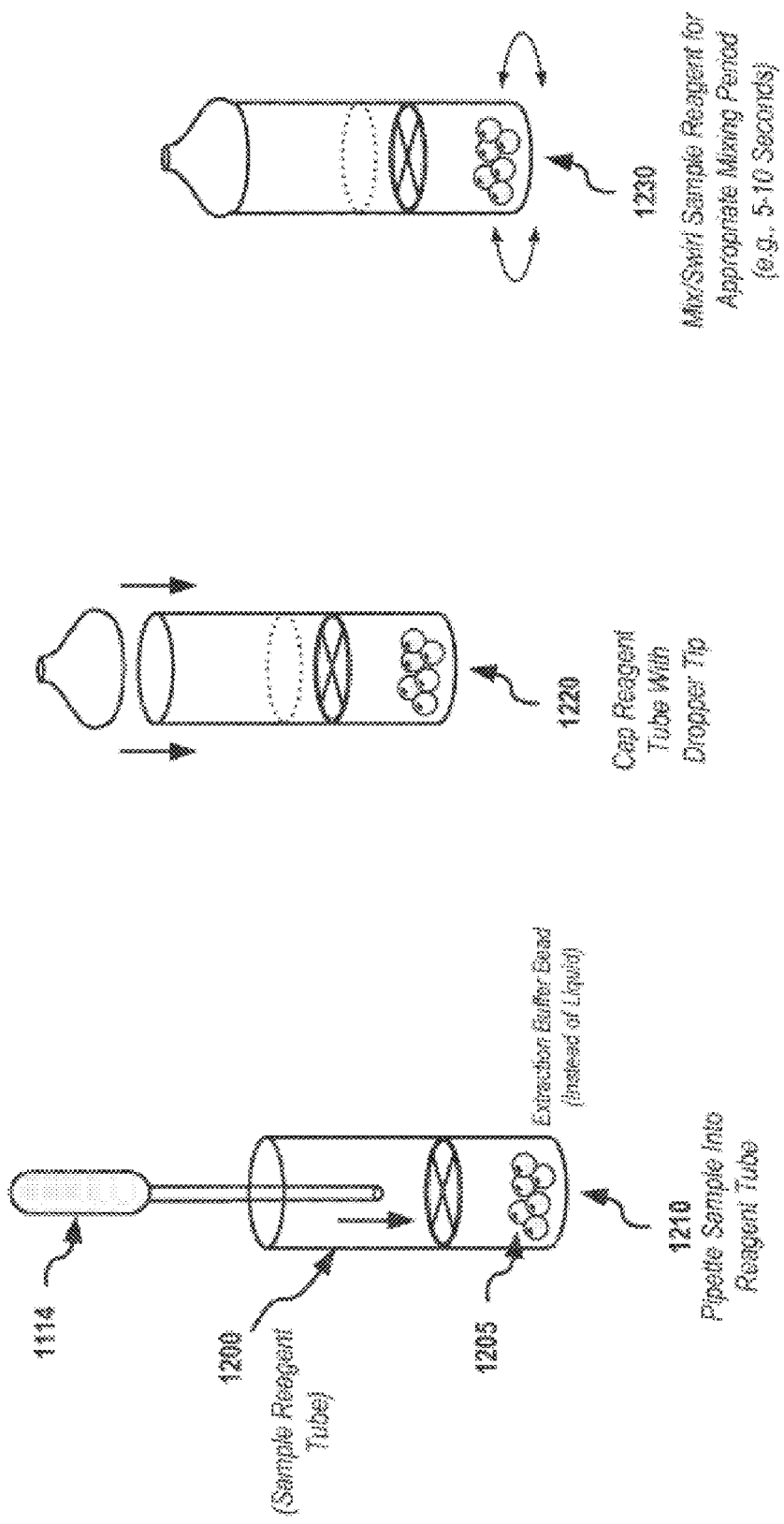

Attention is now directed to FIG. 12, which illustrates use of a sample reagent tube 1200 such as described herein. Tube 1200 may correspond with tubes 200, 600, 700 or 800 described previously. At stage 1210, the sample liquid may be transferred from pipette 1114 to tube 1200. Tube 1200 may contain lyophilized reagent beads 1205 as described. At stage 1220, tube 1200 may be capped for transfer to a test device. At stage 1230, the mixture in tube 1200 may be mixed for an appropriate mixing period, such as, for example, 5-10 seconds.

The extraction solution should be of a sufficient volume to ensure wetting (rehydration) of the reagents beads or pellets and/or to extract the sample. For example, where a dry swab is used as the sample swab, the volume of extraction solution sufficient for extracting or releasing the sample and for wetting the reagents is at least about 70 µl.

The assay medium may include one or more salts, chelators, anticoagulants, detergents, stabilizers, diluents, buffering agents, enzymes, cofactors, specific binding members, labels, bacteriolytic, mucolytic agents and the like.

Figure 13:
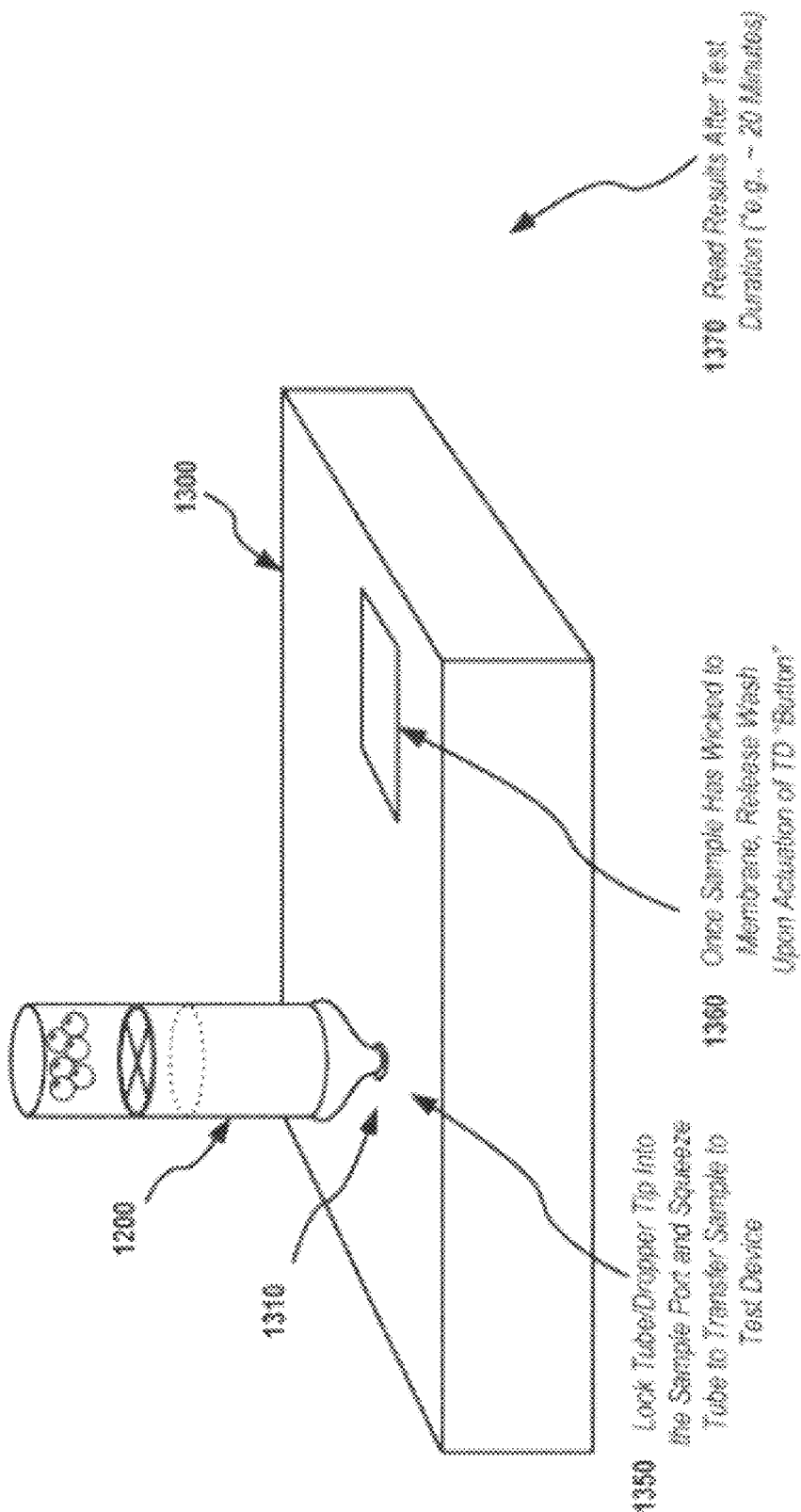

Turning to FIG. 13, the contents of tube 1200 may be transferred to a test device 1300 having a sample port 1310, at stage 1350. The sample may then wick to the test membrane, and, once wicked, a wash may be initiated. The device may then be processed, for example, with the aid of a reader instrument, with a result provided at stage 1370.

In certain embodiments, sample extraction and processing with the reagent beads occurs in a single device, or sample collection device (SCD) as described in WO 2007/098184, which is hereby incorporated by reference. The SCD may comprise one or more sealed chambers, where the seal functions to preclude fluid communication between a second chamber of the SCD. The lower chamber may retain the solid state reagents, and the upper chamber may contain assay media. In some embodiments, the seal comprises a break-away valve, a flapper valve, a twist valve, screw valve, rupturable seal, puncturable seal or breakable valve. In further embodiments, opening a seal can allow the contents of the upper chamber to flow through to the lower chamber(s) of the sample receiving tube. In other embodiments, the upper chamber can contain one or more ampoules that prevent solutions contained therein to flow to the lower chamber, unless pressure is exerted to rupture, puncture or break the ampoule so as to release contents therein.

In one embodiment, the upper chamber comprises a valve that allows controllable release of a solution from the upper chamber. The valve may be any type of valve known in the art and be compatible with the system described herein. Additional valves that can be utilized include a rotary, breakable, stopcock, gate, ball, flapper, needle, butterfly, pinch, bellows, piston, slide, plug, diverter, or actuator valve. For instance, the valve may be a break-away valve, a snap valve, a flapper valve, a twist, screw, rupturable, puncturable or breakable valve. For example, where the valve is a snap valve, the user applies force to the valve stem to break the stem, whereby the breakaway feature allows buffer to enter a sample collection tube and the lower chamber via the stem. In one embodiment, the upper chamber is under positive pressure, such that opening of a valve or breaking of a seal results in an outflow of solution in the upper chamber. In one embodiment, the upper chamber is under sufficient positive pressure such that the solution in the upper chamber flows under pressure to enter the lower chamber via the stem. For example, where the valve is a snap-valve, the user applies force to break the snap-valve stem, and the solution in the upper chamber flows under slight pressure to enter the lower chamber via the stem.

Therefore, where a sample is washed downward via the solutions (e.g., buffer or wash solutions) provided in the upper chamber, a mixture comprising the solutions and the sample is produced that travels down to the lower chamber mixing or reagent component, which lower chamber mixing or reagent component comprises the reagent area with a solid reagent. The solid reagent can be dissolved rapidly by the buffer and the resultant solution can be a mixture of sample that may contain analyte(s) of interest, and the assay reagents (e.g., specific binding agents, label detection and capture probes, etc.). In some embodiments, the SCD can also include a luer lock that locks into a test device for delivery of the reaction mixture for subsequent detection.

In some embodiments, the solution in the upper sealed compartment is a buffer solution. The volume of the solution may be from about 50 µl to about 5 mL, or in other embodiments, about 100 µl to about 500 µl (e.g., about 80, 100, or 120 µl). The solution in the upper chamber may be a sealed compartment, which is punctured, broken or opened via a valve structure, so as to provide fluid communication between the upper chamber and lower chamber. In one embodiment, the upper chamber can be a squeezable bulb that is capable of being compressed (e.g., user applies pressure to the bulb). In some embodiments, the upper chamber is comprised of a bulb component that is a self-contained compartment that includes a solution. Such solutions include extraction, lysis, reagent, buffer or preservative solutions.

In some embodiments, the upper chamber is comprised of a semi-rigid or depressible material. In other embodiments, the upper chamber is comprised of a hard or rigid material. Materials useful for creation of a hard or rigid upper chamber include, for example, hard plastics or glass. The one or more compartments present in an upper chamber can contain a solution, e g, wash buffer, extraction buffer, reagent solution or a combination thereof.

In one embodiment, the sampling assembly is not integrated with the housing containing a sample receiving tube. In such a configuration, the sampling assembly is utilized to collect and deliver a sample to a sample-receiving chamber. The sample-receiving chamber can be opened or closed to allow a sample to be introduced into sample-receiving tube.

It should be understood that any sample-receiving tube disclosed herein can be of a variety of geometric shapes, including cylinder, square, triangle or any polygon, as desired. In some embodiments, the housing can comprise one or more sealable apertures that can be opened to add one or more selected reagents, buffers or wash fluids.

The contents are transferred to a Test Device (TD) for detection. In some embodiments, a Test Device can comprise a body housing a lateral flow membrane, wherein the body provides one or a plurality of windows through which the lateral flow membrane is visible. In various embodiments described herein, a TD comprises a lateral flow membrane that comprises a wicking substrate and an absorbent substrate upstream or downstream of the test zones disposed on said lateral flow membrane. In still other embodiments, the TD comprises a chamber for visualizing or quantifying a bioluminescent reaction.

In general, a TD includes a matrix defining an axial flow path. Typically, the matrix further includes a sample-receiving zone, one or more test zones and one or more control zones. In some embodiments, a test region comprises the test and control zones, which are collectively addressable lines. In one embodiment, downstream of the test strip is disposed an absorbent substrate. In another embodiment, a test membrane can overlap or abut to one or both the wicking substrate and absorptive substrate, respectively. One or more windows through the upper housing permits visualization and reading of the results. The test membrane may further comprise an absorbent zone disposed downstream of the last of an addressable line. In one embodiment, a compartment is disposed upstream of the lateral flow membrane. In another embodiment, a wicking pad is disposed directly below the sample entry aperture.

Suitable materials for manufacturing absorbent substrates include, but are not limited to, hydrophilic polyethylene materials or pads, acrylic fiber, glass fiber, filter paper or pads, desiccated paper, paper pulp, fabric and the like.

In certain embodiments, a sample collection device comprises components that are fit together to produce negative back pressure that allows a solution to be released from the SCD in a uniform manner without a need for external pressure or manipulation of the SCD. For example, seating components of the reagent tube may be made of a hard or rigid material so that the components can form a air-tight seal through force (e.g., force-fit). In one embodiment, an SCD and TD are coupled via an orifice (e g, split septum).

In another embodiment, the distal end of the SCD is open, whereby prior to release of a solution from the upper sealed chamber, the SCD is engaged (e g, by friction fit) into the receiving port of a TD. In such an embodiment, the fluid flow from the distal end of the SCD into the TD need not be regulated by a luer or a valve structure, but fluid flow can be obtained via, for example, by the creation of negative pressure within the TD or a differential pressure between the SCD and TD, gravity or capillary flow.

In another embodiment, the distal end of the SCD does not utilize a valve but rather is open. The SCD may be attached to the test device prior to release of the buffer from the upper chamber. Upon release of the solution from the upper chamber, the sample is released and/or extracted from the collection implement by the solution and mixed with the reagents located in the lower chamber. The mixture then flows to the test device for analysis of the presence of one or more analytes. It is possible to include water-dissolvable membranes within the lower chamber to slow the flow of the mixture out of the SCD onto the test device. Such membranes are conventional and can be designed to permit the retention of the mixture for differing periods of time sufficient to allow mixing and reaction of the reagents and sample analytes.

In some embodiments, the Test Device is shaped to fit (specialized adaptor shape) into the receiving port of a reader. For example, in some embodiments the Test Device fits the reader instrument only after wash buffer has been applied to the membrane, for example, when an upstream actuator has been depressed thus indicating that wash buffer or chase buffer contained therein has been released through the lateral flow membrane. In such embodiments, a specialized adaptor present in the Test Device and Reader provides a means to verify that chase buffer or solution in the upstream chamber of the Test Device has been released and thus indicates that any sample present upstream of the lateral flow membrane is washed through the lateral flow membrane. Thereby, the specialized adaptor provides a "safety means" to prevent reading of unprocessed samples.

The reader is provided to detect a signal from a Test Device as an indication of the presence/absence of analyte(s), such as for example, a UV LED reader. In various embodiments, the signal detected is a fluorescence signal from a label molecule. In further embodiments, the label molecule is a lanthanide, such as europium. In one embodiment, the reader comprises a UV photodiode or a UV laser diode.

In some embodiments, the reader is configured to comprise at least one hard or permanent standard. A hard standard comprises a label molecule emitting a detectable signal. The various suitable labels are described in WO 2007/098184, which is hereby incorporated by reference.

In some embodiments, the sample receiving tube is made of a soft or flexible material. Materials useful for creation of the sample-receiving tube are well known in the art, and include soft plastic. In other embodiments, the sample-receiving tube can be made of a hard or rigid material. Materials useful for creation of a hard or rigid sample-receiving tube are well known in the art, and include, for example, hard plastic (e.g., polypropylene) or glass.

The detectable label may be any substance which is capable of producing a signal detectable by visual or instrumental means. Various labels suitable for use include labels that produce signals through either chemical or physical means. Such labels include enzymes and substrates, chromogens, catalysts, fluorescent or fluorescent-like compounds and/or particles, or aggregates, magnetic compounds and/or particles, chemiluminescent compounds and or particles, and radioactive labels. Other suitable labels include particulate labels such as colloidal metallic particles such as gold-colloidal non-metallic particles such as selenium or tellurium, dyed or colored particles such as a dyed plastic, organic polymer latex particles and liposomes, colored beads, polymer microcapsules, sacs, or other vesicles containing directly visible substances. A visually detectable label is generally used as the label component of the label reagent, thereby providing for the direct visual or instrumental readout of the presence or amount of the analyte in the test sample without the need for additional signal-producing components at the detection sites.

The systems and methods described herein can include an immunoassay device in combination with a reader, particularly a reader with a built-in computer, such as a reflectance and/or fluorescence based reader. Such readers may also contain data processing software employing data reduction and curve fitting algorithms, optionally in combination with a trained neural network for accurately determining the presence and/or concentration of analyte in a biological sample. In one embodiment, a fluorescence reader is configured to comprise an integrated or permanent standard ("hard standard"). The term "hard standard" means that the device for reading a test sample comprises an internal, integrated or permanent standard, against which samples labeled with the same label as that used in the hard standard are read. In one embodiment, the hard standard and the test label comprise a lanthanide (e.g., Europium III).

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present invention is not intended to be limited to the embodiments shown herein but is to be accorded the widest scope consistent with the principles and novel features disclosed herein.

EXAMPLES

Example 1: Evaluation of Modified Crosshair

Because of the observation that the input volume of assay medium (e.g., VTM) resulted in reagent solution hanging-up in the crosshairs of the tube upon inverting the tube, a design modification of the crosshair structure was created. The impact of this modified tube on reagent solution hang-up and bead retention was evaluated.

The center of the crosshair structure in the tube was snipped out using scissors. This created a 4-line-structure that is discontinuous. The lines are about 2.5 to 3 mm in length. The center opening is less than 3 mm which should be sufficient to retain the lyophilized beads (~2 mm).

This example employed lyophilized Europium and pRNA reagent beads, as well as Pluronic/NaCl and TDOC/Casein/BSA extraction beads.

Each of the four reagent beads was placed into the tube with crosshairs, and 120 μl of VTM added to beads, and agitated to dissolve. Tubes were inverted and observed for fluid hang-up. The recovered fluid volume was weighed. As a result, it was found that the modified crosshairs retained the beads, and no hang-up of sample was observed, although there was residual fluid loss of about 20 μl. In some samples, the liquid continued to drip for from 3 to 7 seconds.

The experiment was repeated using 100 μl of input volume. Again, 20 μl of residual loss was observed, although the lower volume has a higher CV than 120 μl. Reuse of tips results in occasional drip formation.

In conclusion, the 4-line modified crosshair in the tube body prevents hang-up of sample liquid regardless of input volume. 100 μl of input volume allows 76 to 83 μl of sample delivery volume 120 μl of input volume allows 94 to 103 μl sample delivery volume. The 4-line modified body still retains lyophilized beads in the cap.

Example 2: Evaluation of Crosshair Radius

This example evaluates the volume delivery for caps with a greater radius inside. The intent is to allow less retention of sample liquid in the cap where the tube is inverted to draw the sample into the tip. The caps are to be evaluated with first use tips and body tubes that either have the original crosshair structure or have the center crosshair snipped out, creating a 4-prong rib design. This example uses 100 μl or 120 μl of VTM as diluent, and lyophilized reagent beads as described.

Liquid beading formed on all inside surfaces of tubes from solution running down upon tube being inverted.

Hangup volume in crosshair design occurred either at quadrants of crosshairs and/or rim of inverted cap, and at junction of cap and bottom of tube.

Delayed drip formation was manually corrected.

Conclusion: the open rib design generated a higher volume delivery compared to the crosshair design with lower CVs. Residual loss was 17-23 μl without sample hangup in the cap. 120 μl yielded lower CV and liquid retention compared to 100 μl input volume. Rev X 1 cap performs similarly in terms of volume retention compared to a previous lot of caps—volume retention around 20 μl.

Example 3: Evaluation of Modified Rib Retainers for Liquid Hang-Up

This example evaluates the volume delivery, bead retention and liquid hang-up of the Rev-X1 body tube with rib retainers. This version of the body tube is the first manufacture of the modified tube disallowing liquid hang-up when the tube is inverted to deliver the sample. The example tests for hang-up of 120 μl of VTM.

Observations: The rib design molded into the body tube was intact and appeared structurally strong. The buttressed ribs resembled the modified crosshairs from previous examples. Any flashing from the mold was microscopic. The cap and tip fitted securely onto the body tube. The tip did require some care (direct pressure) to avoid bending the tube. Results were similar to previous experiments.

The invention claimed is:

1. A method for detecting an analyte, comprising:
    applying a volume of liquid sample suspected of containing the analyte to an apparatus retaining solid-state reagents, wherein the apparatus comprises a compartment containing the solid-state reagents in bead or pellet form, wherein the compartment has an opening defined by ribs having a rounded cross-section configured to retain the solid-state reagents while reducing hang-up of liquid sample to less than 20% of the volume of the liquid sample, and wherein the solid-state reagent comprises at least one immunoreagent comprising a capture moiety for a capture moiety partner;
    delivering the liquid sample to a lateral flow membrane configured to interface with the apparatus;
    generating a signal by the analyte in the sample on the lateral flow membrane; and
    detecting a signal on the lateral flow membrane, wherein the signal indicates the presence of the analyte in the sample, wherein the solid state reagents comprises at least one immunoreagent against the analyte.

2. The method of claim 1, the apparatus comprises a tube having the compartment retaining the solid-state reagents.

3. The method of claim 2, wherein the liquid sample suspected of containing the analyte is added to the apparatus by pipette, wherein the apparatus is in the form of a tube, wherein the method further comprises: fitting a cap over the opening of the tube; and inverting the tube to deliver the liquid sample and solubilized reagents onto the lateral flow membrane.

4. The method of claim 1, wherein the capture moiety is a pDNA, pRNA, streptavidin or biotin.

5. The method of claim 1, wherein the rib diameter is from about 0.01 to about 0.06 inches.

6. The method of claim 1, wherein the rib diameter is about 0.03 inches.

7. The method of claim 1, wherein the ribs protrude from the end of the tube.

8. The method of claim 1, having 3 or 4 ribs.

9. The method of claim 8, wherein the ribs extend radially and are evenly spaced around the circumference of the opening.

10. The method of claim 1, wherein the ribs do not meet.

11. The method of claim 1, wherein the solid-state reagents are lyophilized or dried in the form of pellets or beads.

12. The method of claim 1, wherein the solid-state reagents are reagents conjugated to beads or pellets.

13. The method of claim 1, wherein the at least one immunoreagent comprises a detectable moiety.

14. The method of claim 1, wherein the immunoreagent is against an analyte of interest, and wherein the analyte of interest comprises biomarkers associated with a condition related to any body tissue, toxins, allergens, organic compounds, proteins, peptides, microorganisms, bacteria, amino acids, nucleic acids, nucleic acids, carbohydrates, hormones, steroids, vitamins, drugs, pollutants, pesticides, and metabolites of or antibodies to any of the aforementioned substances.

15. The method of claim 1, wherein the apparatus interfaces with a device comprising the lateral flow membrane, to deliver the solubilized reagents and liquid sample from the compartment.

16. The method of claim 1, wherein the signal is read using a fluorescent or visible signal reader.

* * * * *